United States Patent [19]
Martin

[11] Patent Number: 5,405,341
[45] Date of Patent: Apr. 11, 1995

[54] CATHETER WITH MULTIPLE LUMENS

[75] Inventor: Geoffrey S. Martin, Mississauga, Canada

[73] Assignee: Med-Pro Design, Inc., Mississauga, Canada

[21] Appl. No.: 70,832

[22] Filed: Jun. 3, 1993

[51] Int. Cl.⁶ ............................................ A61M 25/00
[52] U.S. Cl. ...................................... 604/284; 604/43; 604/164; 604/280
[58] Field of Search ................. 604/284, 43, 175, 280, 604/281, 264, 249, 256, 53, 174, 44, 45, 28, 52, 93, 51, 164, 282, 283, 236, 40, 905, 96; 606/191, 192, 194

[56] References Cited

U.S. PATENT DOCUMENTS

| | | | |
|---|---|---|---|
| 4,315,512 | 2/1982 | Fogarty | 606/194 |
| 4,385,631 | 5/1983 | Uthmann | 604/284 |
| 4,619,643 | 10/1986 | Bai | 603/43 |
| 4,643,711 | 2/1987 | Bates | 604/4 |
| 5,041,083 | 8/1991 | Tsuchida et al. | 604/43 |
| 5,087,247 | 2/1992 | Horn et al. | 604/98 |
| 5,267,958 | 12/1993 | Buchbinder et al. | 604/96 |

FOREIGN PATENT DOCUMENTS

WO9214500 9/1992 WIPO.

Primary Examiner—C. Fred Rosenbaum
Assistant Examiner—V. Alexander
Attorney, Agent, or Firm—Rogers & Scott

[57] ABSTRACT

The invention provides a catheter assembly having an elongate main body extending longitudinally between proximal and distal ends. A tip structure is attached to the distal end of the main body and also extends longitudinally. The main body and tip structure combine to define side-by-side intake and return lumens and the intake lumen terminates at a transverse intake opening at the distal end of the main body. The return lumen terminates at the distal end of the tip structure at a transverse return opening and a side opening is provided adjacent the return opening. A tubular applicator passes through the intake lumen, through the side opening and into the return lumen. This permits the assembly to be passed over a guide wire by engaging the wire inside the tubular applicator.

20 Claims, 2 Drawing Sheets

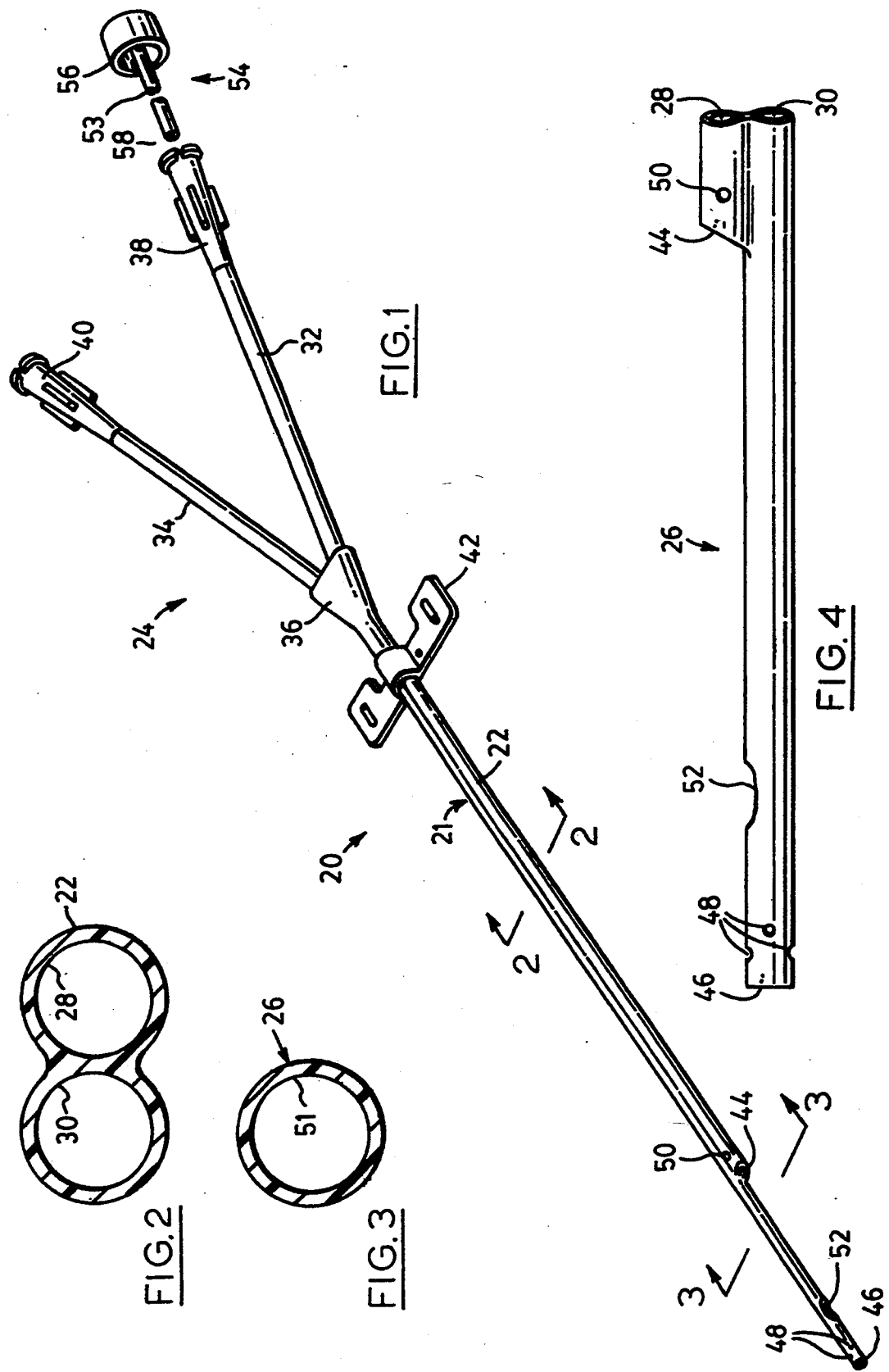

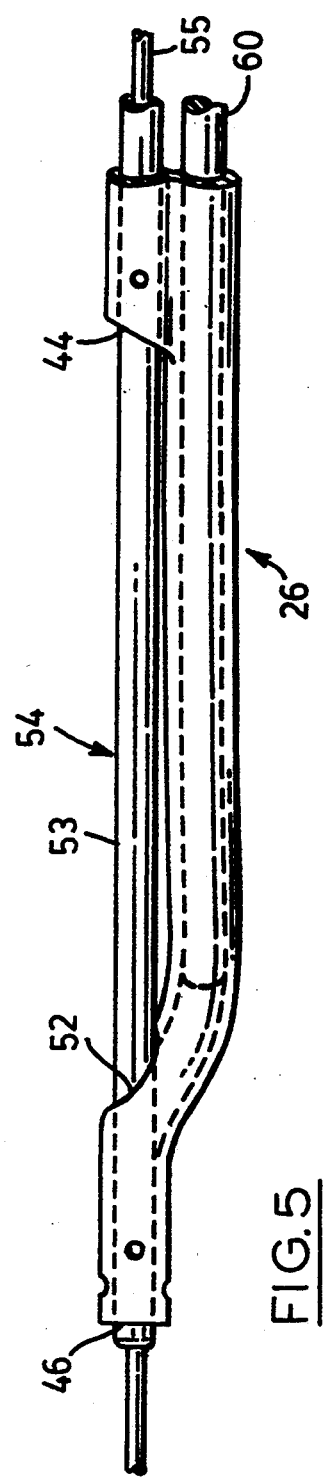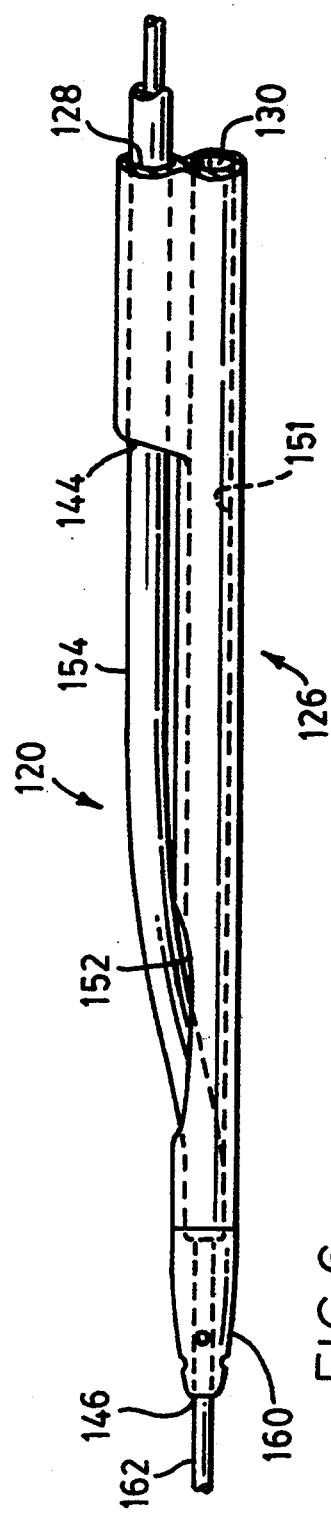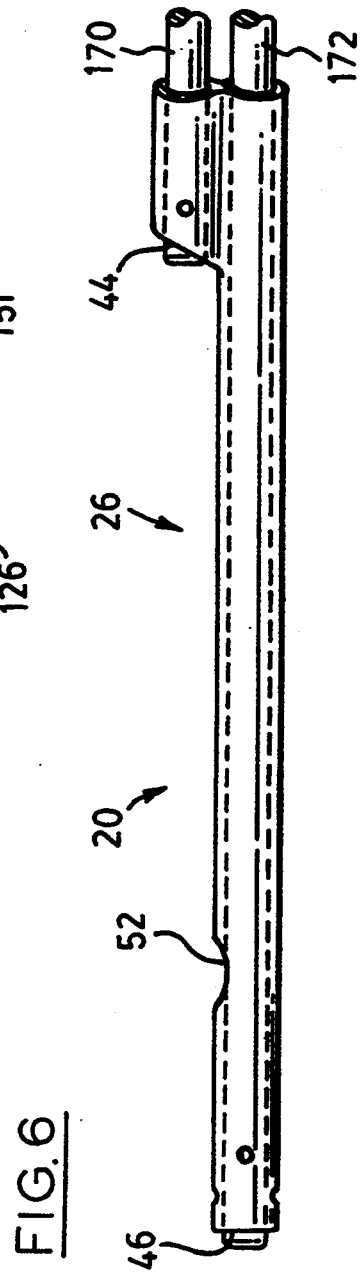

CATHETER WITH MULTIPLE LUMENS

FIELD OF THE INVENTION

This invention relates to a dual lumen catheter and more particularly to such a catheter which is to be engaged into body tissue over a guide wire of the Seldinger type. The catheter is particularly useful in haemodialysis treatments.

BACKGROUND OF THE INVENTION

Although this invention will be described with reference to use in haemodialysis, it will be appreciated that the various forms of the invention can be used wherever dual flow is required.

Haemodialysis can be defined as the temporary removal of blood from a patient for the purpose of extracting or separating toxins from the blood and returning the cleansed blood to the same patient. Haemodialysis is indicated in patients where renal impairment or failure exists, that is, in cases where the blood is not being cleansed naturally by the kidneys.

In the case of chronic renal impairment or failure, haemodialysis is carried out on a repetitive basis. For example, in end stage kidney disease where transplantation of kidneys is not possible or for medical reasons is contra-indicated, the patient will have to be dialysed about 100 to 150 times per year. This can result in several accesses to the bloodstream to enable the act of haemodialysis to be performed over the remaining life of the patient. The fact that dual flow is required to conduct haemodialysis means that there must be two distinct channels, one to remove the blood from the patient, and the other to return it. This was achieved in one approach by two insertions, each insertion carrying a single lumen catheter. Subsequently, dual lumen catheters have been inserted both by surgical cut-down techniques and also by engagement over a Seldinger wire using a technique developed by Dr. S. I. Seldinger which was presented at the Congress of the Northern Association of Medical Radiology at Helsinki in June of 1952. The technique remains current and is used widely.

It is clear that if a dual lumen catheter is to be inserted over a wire, the leading end of the catheter must be arranged to permit this engagement through tissue without tearing or snagging the tissue. An earlier approach to solving this problem was to make the dual lumen catheter of a co-axial construction which allowed the tip to be tapered for engagement through the tissue over the existing wire. Other catheters were developed where the lumens are arranged in side-by-side configuration and a tip formed especially to close off one lumen at a point spaced from the tip so that a tip could be formed around the return lumen to facilitate engagement over the wire. Structures of this kind can be found in U.S. Pat. Nos. 4,619,643, 4,583,968, 4,568,329, 4,543,087, 4,692,141, and 4,568,329. One of the disadvantages of this arrangement is that the structures result in stiff tips which although facilitating dilation of body tissue as the catheter is moved over the wire, they tend to result in relatively stiff structures inside the blood vessel after placement. As a result such catheters are useful only for temporary access.

If a catheter is to be used for extended placement, it must be extremely flexible to avoid stress in the blood vessel, and as much as possible, permit the catheter to move in the blood flow to minimize the possibility of the catheter remaining in pressure contact with the wall of the blood vessel at one spot for prolonged periods. It is also true, that if a catheter is designed for prolonged placement, then the very flexibility that is desirable for prolonged placement creates limitations for engagement over the Seldinger wire because the catheter lacks sufficient strength to dilate the tissue.

In summary, although there have been significant developments in the structures of dual lumen catheters with the lumens arranged in side-by-side configuration, these structures have been limited in their usefulness primarily because of the difficulties of meeting both design criteria required for placement by the Seldinger technique and the somewhat conflicting criteria which must be met for prolonged placement.

A further consideration in the design of dual lumen catheters is the positioning of the intake and return openings. In catheters of the type where the tip has been formed to dilate tissue as the catheter slides over a Seldinger wire, the intake openings are generally on the side of the catheter. This can result in the catheter being drawn by suction forces towards the blood vessel wall and blood flow will then be cut off. It is therefore desirable to arrange the intake opening to be at the end of the intake lumen with the opening extending generally transversely with respect to the longitudinal extent of the catheter. It is very unlikely that the blood vessel will occlude such an opening so that there is a better likelihood of continuous intake flow. On the other hand, this results in a catheter contour which is less than desirable for sliding over a Seldinger wire.

It is one of the objects of the present invention to provide a catheter having side-by-side dual lumens with the intake opening arranged generally transversely with respect to the longitudinal extent of the catheter and which can be engaged over a Seldinger wire.

It is a further object of the invention to provide a catheter for prolonged placement which has the necessary flexibility characteristics and which can be engaged over a Seldinger wire.

SUMMARY OF THE INVENTION

Accordingly, in one of its aspects the invention provides a catheter assembly having an elongate main body extending longitudinally between proximal and distal ends. A tip structure is attached to the distal end of the main body and also extends longitudinally. The main body and tip structure combine to define side-by-side intake and return lumens and the intake lumen terminates at a transverse intake opening at the distal end of the main body. The return lumen terminates at the distal end of the tip structure at a transverse return opening and a side opening is provided adjacent the return opening. A tubular applicator passes through the intake lumen, through the side opening and into the return lumen. This permits the assembly to be passed over a guide wire by engaging the wire inside the tubular applicator.

This and other aspects of the invention will be apparent from the following description taken in combination with the drawings, in which:

BRIEF DESCRIPTION OF THE DRAWINGS

FIG. 1 is a diagrammatic isometric view of a catheter looking from the proximal end towards the distal end;

FIG. 2 is a sectional view on line 2—2 and drawn to a larger scale;

FIG. 3 is a view similar to FIG. 2 and drawn on line 3—3 of FIG. 1;

FIG. 4 is a side view in the direction of the arrow 4 shown in FIG. 1 and drawn to a larger scale;

FIG. 5 is a view similar to FIG. 4 and showing an applicator and wire, and a rod engaged in the catheter;

FIG. 6 is a view similar to FIG. 5 and showing an alternative embodiment of the catheter assembly; and FIG. 7 is a further view of the catheter shown in FIG. 4 after insertion and containing mandrels.

DETAILED DESCRIPTION OF A PREFERRED EMBODIMENT OF THE INVENTION

Reference is made to FIGS. 1 and 2 which illustrate a preferred embodiment of catheter assembly according to the invention and identified generally by the numeral 20. A catheter 21 as shown in FIG. 1 has a main body 22 which terminates at its proximal end in a coupling structure indicated generally by the numeral 24 and at its other end, (i.e. at its distal end) in a tip structure indicated generally by the numeral 26.

As seen in FIG. 2, the cross-section of the main body 22 is generally kidney shaped and includes a first or intake passage 28 and a second or return passage 30. These passages lead from the coupling structure 24 which includes an intake tube 32, return tube 34, and a connector 36 providing fluid communication between the respective passages 28, 30 (FIG. 2) and the tubes 32, 34. The tubes 32, 34 are very flexible and have at their proximal ends respective luer connectors 38, 40 as is conventional in the art. Commonly the tubes 32, 34 would also include pinch clamps and these have been omitted to simplify the drawing.

The main body also carries a suture wing structure 42 located against the connector 36 and at its other end, the main body terminates at an intake opening 44 providing access to the passage 28. The tip structure 26 forms a continuation of the passage 30 and ends at a return opening 46 at the distal end of the catheter. As is conventional in catheter structures for use in haemodialysis, a number of side holes 48 are provided adjacent the return opening 46 and similarly holes 50 are provided adjacent the intake opening 44.

Reference is next made to FIGS. 3 and 4 to better describe the tip structure 26. It will be seen in FIG. 3 that the cross-section is round and defines a third passage 51. The exact shape of the tip structure is the result of some post-forming after the blank for the main body has been modified by cutting back the material defining the passage 28 so that only the tip structure projects beyond the intake opening 44. The second passage 30 (FIG. 2) and the third passage are aligned to combine to form a return lumen and the first passage 28 defines an intake lumen.

As seen in FIG. 4, the tip structure includes a side opening 52 on the side of the tip structure nearest the intake opening 44. The opening 52 is preferably in the form of a slit or slot but for the purposes of drawing, the opening is shown formed by cutting away material. The slit is preferred, particularly if the material of the catheter is sufficiently flexible as will be the case in most instances.

The purpose of the opening 52 is to facilitiate use of a tubular applicator 54 shown generally in FIG. 1.

Reference is now made to FIGS. 4 and 5. The applicator 54 has a cap 56 which fits on the luer fitting 38 and when in that position, a main portion 53 of the applicator will then project through the return opening 46 in the tip structure 26 as seen in FIG. 5. The applicator is entered through the tube 32, connector 36, and through the passage 28 in the main body 22, so that it will project from the intake opening 44 at the end of the passage 28. The applicator then extends from opening 44, through side opening 52 and through part of the third passage 51 (FIG. 3) from the side opening 52 to the return opening 46 ready to engage the catheter assembly so formed over a guide wire 55 seen in FIG. 5 for purposes of illustration.

As seen in FIG. 5, the flexibility of the tip structure 26 is such that the applicator 54 has the main portion 53 of the applicator 54 entered through the side opening 52 and continues within the return lumen exiting at the return opening 46. The length of the applicator main portion 53 is chosen so that with the cap 56 engaged with the luer connector 38, the distal end of portion 53 just projects beyond the return opening 46 to present a stepped profile for dilating tissue. It will be evident that the cap 56 and luer connector combine to act as a locator which positions the applicator in the catheter 21.

Reference is next made to FIG. 6 which illustrates a second embodiment of tip structure. As seen in FIG. 6, a tip structure 126 is provided having an intake or first passage 128 and second passage 130 which meets a third passage 151 in the tip structure to complete the intake lumen. An opening or slit 152 is provided in the tip structure so that an applicator 154 can pass through this opening into the return lumen. The passage 151 in the tip structure includes a part extending from the side opening 152 to the return opening 146. This part is shaped externally to define a slight taper 160 about a part of the passage of reduced diameter to fit around a wire 162. This part of reduced reduced diameter meets the remainder of the passage 151 at a socket 164 where the change in diameter provides a shoulder for engagement by the distal end of the applicator 154. As a result the applicator can be used to push the very flexible catheter guided by the wire 162.

In use the catheter and the applicator will be preassembled. The assembly will be completed in the case of catheter 21 (FIG. 1) by including a flexible rod 60 (FIG. 5) used to stiffen the tip structure 26. This rod will be pushed until it meets resistance and then held there. The whole assembly is then slipped along wire 55 which has been pre-positioned in a blood vessel for the purpose. As the catheter assembly engages tissue the outer surfaces will dilate the tissue and eventually the smooth main body will be resident in the resulting tunnel through the tissue. The rod 60, applicator 54 and lastly, wire 55 will be removed leaving the catheter 21 (FIG. 1) for use in conventional fashion.

The catheter also has advantages which come into play when the catheter is in place between treatments. It is common to use an anti-coagulant (commonly heparin) and to fill the catheter with this material to minimize the risk of stagnant blood clotting inside the catheter. In practice, the heparin does tend to migrate into the bloodstream to some extent and is of course displaced by blood. For this and other reasons, an alternative to the use of an anti-coagulant would be preferred.

Reference is now made to FIG. 7 which shows catheter 20 containing a pair of fitted occlusion mandrels 170, 172. These are positioned in the lumens to project slightly and to occlude the lumens entirely. There is then no need to use an anti-coagulant.

Catheter assembly 120 shown in FIG. 6 will be used in similar fashion. However because the applicator 154 meets a socket in the tip structure, the applicator can be used to push the catheter and it may be possible to do this without the need for a rod such as rod 60 (FIG. 5).

It will be evident from the foregoing description that variations can be made to the catheter, and in particular to the tip structure. Two examples are given and others are possible. In practice, because both the applicator and the tip structure will have some flexibility, the actual appearance may not be exactly as drawn. For simplicity, FIG. 5 shows all the flexibility in the tip structure whereas FIG. 6 shows all the flexibility in the applicator. It will be evident that this makes for a simplified drawing but does not accurately represent the shape. Nevertheless, it will be clear that the applicator performs the purpose of closing off the intake openings 44, 144 and combines with the tip structure to provide a smooth surface suitable for dilating and passing through tissue. Of course the tip structure will pass entirely through the tissue leaving the main body 22 (FIG. 1) extending through the tissue and into the blood vessel. The smooth shape of the main body will permit the tissue to close around the main body and essentially seal the tissue to the main body as is conventional in the art.

The material of choice for vascular access catheters made according to the invention is polyurethane. Such catheters would use such a material having a 60–65D durometer and the insertion applicator would be of a stiffer form of polyurethane sufficient to perform the designed function.

These and other variations are within the scope of the invention as described and claimed.

I claim:

1. A catheter assembly for engagement over a wire to enter the catheter by sliding the catheter along the wire, the assembly comprising:
   a main body extending longitudinally and defining first and second passages, a first of the passages terminating at a distal end of the body at an intake opening extending generally orthogonally with respect to the main body and forming an intake lumen;
   a proximal end coupling structure having a connector attached to the main body and a pair of tubes including coupling devices at their respective proximal ends and the tubes being connected at their distal ends to the connector such that selected ones of the tubes are coupled for fluid flow to respective ones of the passages;
   tip structure extending longitudinally from the distal end of the main body and forming a continuation of the second passage to form with this passage a return lumen, the tip structure defining a distal end return opening and a side opening on a side of the tip structure closest to the intake lumen;
   a tubular applicator extending through the one of said tubes, through the connector and the intake lumen, through said intake opening and through said side opening, and then inside a portion of the return lumen between the side opening and the return opening whereby the assembly can be slid over the wire by containing the wire in the applicator with the applicator exposed between the side opening and the intake opening to present a smoother exterior for insertion through body tissue.

2. A catheter assembly as claimed in claim 1 in which the passages are substantially round in cross-section.

3. A catheter as claimed in claim 1 in which the applicator includes a locator in engagement with a corresponding one of said coupling devices when the applicator extends to or slightly outside the return opening.

4. A catheter as claimed in claim 1 in which the side opening is a slit.

5. A catheter assembly as claimed in claim 1 and further confirming a pair of occlusion mandrels for engagement in the lumens between treatments to occlude the lumens to minimize the risk of containing stagnant blood in the catheter.

6. A catheter assembly for engagement over a wire to enter the catheter by sliding the catheter along the wire, the assembly comprising:
   a main body extending longitudinally and defining first and second passages, a first of the passages terminating at a distal end of the body at an intake opening extending generally orthogonally with respect to the main body and forming an intake lumen;
   a proximal end coupling structure having a connector attached to the main body and a pair of tubes including coupling devices at their respective proximal ends and the tubes being connected at their distal ends to the connector such that selected one of the tubes are coupled for fluid flow to respective ones of the passages;
   tip structure extending longitudinally from the distal end of the main body and forming a continuation of the second passage to form with this passage a return lumen, the tip structure defining a distal end return opening and a side operating on a side of the tip structure closest to the intake lumen, said continuation of the second passage defining a socket adjacent the side opening; and
   a tubular applicator extending through the one of said tubes, through the connector and the intake lumen, through said intake opening and through side opening, and inside a portion of the tip structure terminating in the socket whereby applicator is exposed between the side opening and the intake opening to present a smoother exterior for insertion through body tissue by sliding the applicator with the catheter over the wire.

7. A catheter assembly as claimed in claim 6 in which the passages are substantially round in cross-section.

8. A catheter as claimed in claim 6 in which the side opening is a slit.

9. A catheter assembly for engagement to guide the catheter through body tissue, the catheter assembly comprising:
   a dual lumen catheter having an intake lumen terminating at a distal end in an intake opening extending transversely with respect to the first lumen; a return lumen extending side-by-side with the first lumen and extending beyond said opening to terminate at a return opening extending transversely with respect to the return lumen; a tip structure extending between the intake opening and the return opening and containing a portion of the return lumen, the tip structure defining a side opening adjacent the return opening; and a coupling structure at the proximal ends of the first and second lumens to make connection to the assembly; and
   a tubular applicator extending through the first lumen, through said intake opening and through said side opening into the second lumen whereby the applicator is exposed between said intake and side openings to present a smoother external profile and the assembly can be slid over a guide wire engaged in the applicator and through the body tissue.

10. A catheter assembly as claimed in claim 9 in which the assembly further includes a flexible rod engaged in the second lumen.

11. A catheter as claimed in claim 9 in which the applicator includes a locator in engagement with a corresponding one of said coupling devices and the applicator is at or slightly outside the return opening.

12. A catheter assembly as claimed in claim 9 in which the second lumen includes a section of reduced cross-section between the side opening and the return opening so that the end of the applicator will engage this section to facilitate pushing the catheter assembly over the guide wire.

13. A catheter as claimed in claim 9 in which the first and second lumens are substantially round in cross-section.

14. A catheter as claimed in claim 9 in which the side opening is a slit.

15. A catheter assembly comprising:
an elongate main body extending longitudinally and having proximal and distal ends;
a tip structure attached to said distal end and extending longitudinally;
the main body and tip structure combining to define side-by-side intake and return lumens, the intake lumen terminating at a transverse intake opening at the distal end of the main body and the return lumen terminating at a transverse return opening at the distal end of the tip structure;
the tip structure defining a side opening adjacent the return opening;
a tubular applicator passing through the intake lumen, through the intake opening, through the side opening, and into the return lumen whereby the applicator is exposed between said intake and side openings to present a smoother external profile and the assembly may be passed over a guide wire placed in body tissue by engaging the wire inside the tubular applicator.

16. A catheter assembly as claimed in claim 15 in which the assembly further includes a flexible rod engaged in the second lumen.

17. A catheter assembly as claimed in claim 15 in which the second lumen includes a section of reduced cross-section between the side opening and the return opening so that the end of the applicator will engage this section to facilitate pushing the catheter assembly over the guide wire.

18. A catheter assembly as claimed in claim 17 in which the applicator includes a locator in engagement with a corresponding one of said coupling devices and the applicator is at or slightly outside the return opening.

19. A catheter assembly as claimed in claim 15 in which the first and second lumens are substantially round in cross-section.

20. A catheter assembly as claimed in claim 15 in which the side opening is a slit.

* * * * *